(12) United States Patent
Olsen et al.

(10) Patent No.: US 11,583,431 B2
(45) Date of Patent: Feb. 21, 2023

(54) KIT OF PARTS AND A COMPLEMENTARY-MATERIAL ELEMENT FOR AN OSTOMY APPLIANCE

(71) Applicant: Coloplast A/S, Humlebaek (DK)

(72) Inventors: Henrik Olsen, Copenhagen (DK); Joergen Daucke von Barner, Struer (DK); Kristoffer Hansen, Naerum (DK); Richard Morgan Hickmott, Helsingoer (DK); Tune Bjarke Bonne, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 77 days.

(21) Appl. No.: 16/761,821

(22) PCT Filed: Nov. 7, 2018

(86) PCT No.: PCT/DK2018/050289
§ 371 (c)(1),
(2) Date: May 6, 2020

(87) PCT Pub. No.: WO2019/091532
PCT Pub. Date: May 16, 2019

(65) Prior Publication Data
US 2020/0306073 A1 Oct. 1, 2020

(30) Foreign Application Priority Data
Nov. 8, 2017 (DK) .......................... PA 2017 70838

(51) Int. Cl.
*A61F 5/443* (2006.01)
*A61F 5/44* (2006.01)

(52) U.S. Cl.
CPC ............ *A61F 5/443* (2013.01); *A61F 5/4404* (2013.01)

(58) Field of Classification Search
CPC ........ A61F 5/443; A61F 5/4404; A61F 5/445; A61F 13/42; A61L 15/42; Y10S 252/96
See application file for complete search history.

(56) References Cited

U.S. PATENT DOCUMENTS 3,908,658 A * 9/1975 Marsan ................. A61L 24/043
604/336
5,051,259 A * 9/1991 Olsen ................... A61F 13/0213
428/355 R
(Continued)

FOREIGN PATENT DOCUMENTS

CN 105163694 A 12/2015
EP 0413250 A1 2/1991
(Continued)

*Primary Examiner* — Philip R Wiest
*Assistant Examiner* — Alessandro R Del Priore
(74) *Attorney, Agent, or Firm* — Coloplast Corp., Coloplast A/S; Nick Baumann

(57) ABSTRACT

Disclosed is a complementary-material element (22) attachable to a base plate (24) of an ostomy appliance (20) and including a first entity (30) and a second entity (32). The entities comprise different material compositions. The material composition of the second entity comprises a neutralizer which is released from the complementary-material element in response to moisture, thereby neutralizing the damaging effects of stomal output.

16 Claims, 8 Drawing Sheets

(56) References Cited

U.S. PATENT DOCUMENTS

| | | | |
|---|---|---|---|
| 2003/0004477 A1* | 1/2003 | Nielsen | A61F 5/448 604/336 |
| 2010/0204665 A1* | 8/2010 | Stroebech | A61F 5/445 604/344 |
| 2012/0165767 A1 | 6/2012 | Abrams | |
| 2017/0007440 A1 | 1/2017 | Moavenian | |
| 2019/0083677 A1* | 3/2019 | Pearce | A61L 24/0094 |

FOREIGN PATENT DOCUMENTS

| | | | | |
|---|---|---|---|---|
| EP | 0998247 | A1 | 4/1998 | |
| EP | 1679086 | A2 | 7/2006 | |
| EP | 1736136 | A1 * | 12/2006 | A61K 36/886 |
| EP | 1736136 | A1 | 12/2006 | |
| EP | 1322348 | B1 | 11/2009 | |
| EP | 2654632 | B1 | 9/2016 | |
| GB | 1256866 | A | 12/1971 | |
| GB | 1328764 | A | 9/1973 | |
| GB | 2418861 | * | 7/2004 | A61F 5/443 |
| GB | 2418861 | A1 | 4/2006 | |
| GB | 2534012 | * | 5/2015 | A61F 5/445 |
| JP | 2001170159 | A | 6/2001 | |
| RU | 2011147047 | A | 5/2013 | |
| WO | 9603167 | A1 | 2/1996 | |
| WO | 06038025 | A1 | 4/2006 | |
| WO | 13130566 | A2 | 9/2013 | |

\* cited by examiner

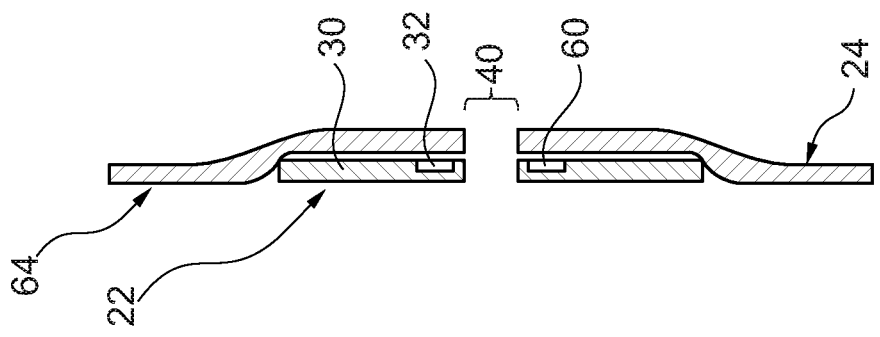
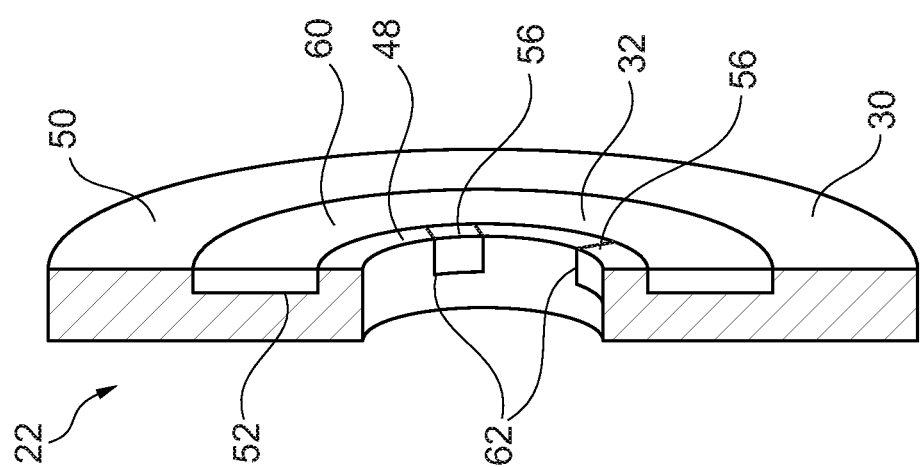
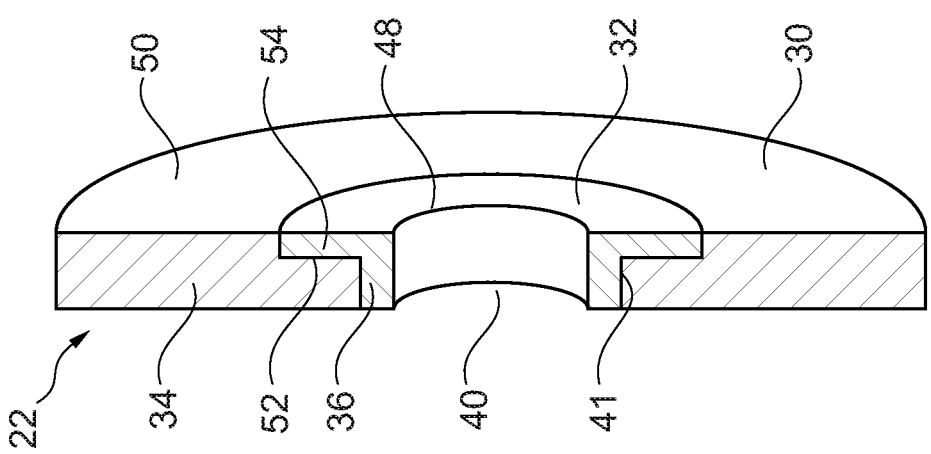

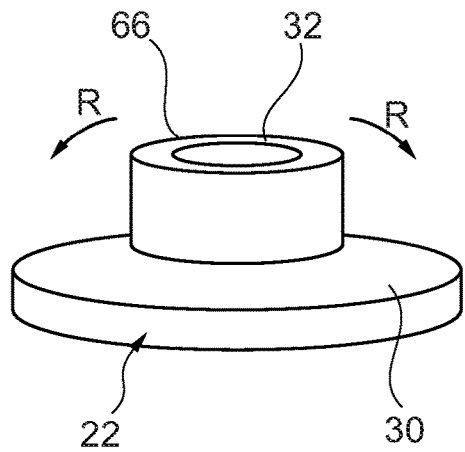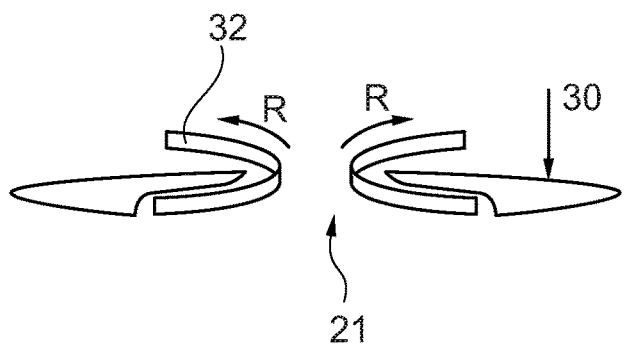
Fig. 5A  Fig. 5B
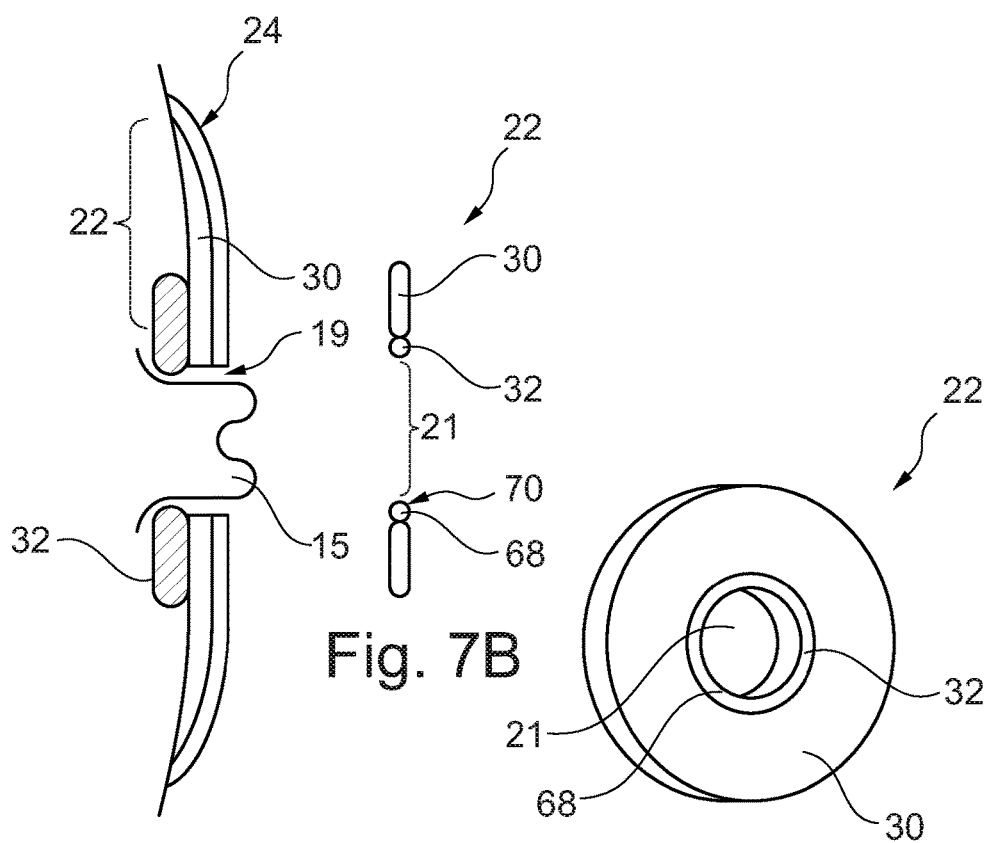
Fig. 6  Fig. 7B  Fig. 7A

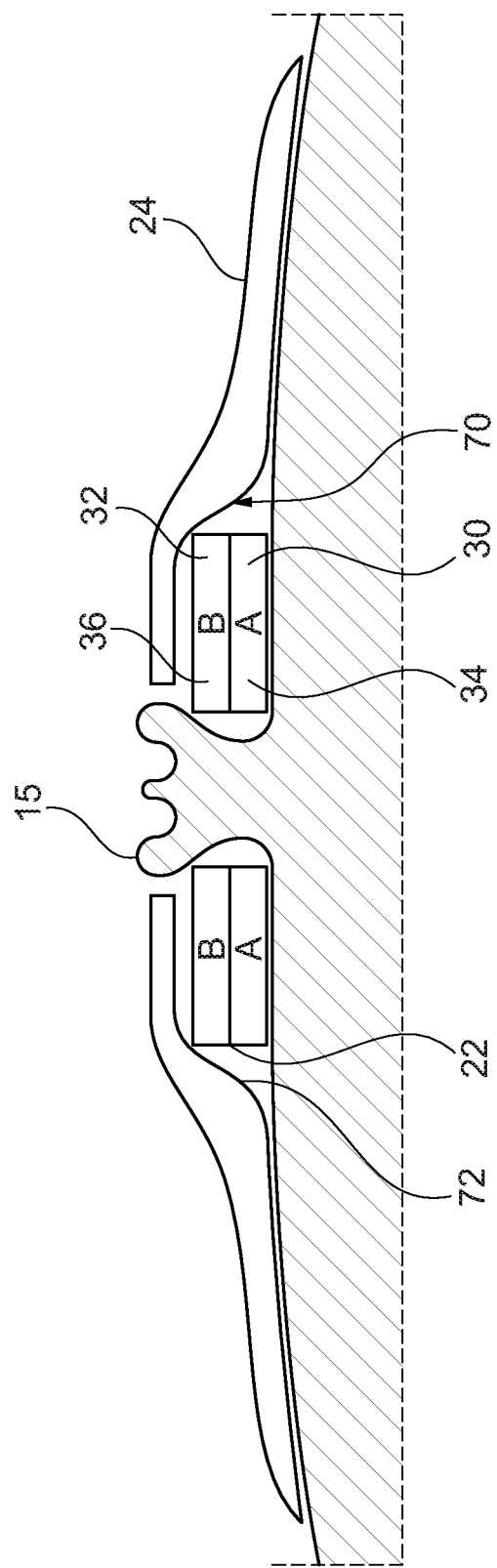

KIT OF PARTS AND A COMPLEMENTARY-MATERIAL ELEMENT FOR AN OSTOMY APPLIANCE

BACKGROUND

Stomal output often contains body fluids and visceral contents that are aggressive to both the skin of a user and to ostomy devices, in particular these have a detrimental effect on the efficiency and integrity of the adhesive materials that are applied to attach the ostomy device to the user's skin surface. Some ostomists may choose or have to wear their device for prolonged periods of time. For users in general, and particularly for these ostomists safe, reliable and efficient ostomy devices are highly desirable. Numerous attempts have been made to provide ostomy devices to meet such demands, e.g. the demand of prolonged wear time, but the provision of sufficient efficiency to achieve a satisfactory long wear time of ostomy devices continues to be an unmet need.

Ostomists (ostomy appliance users) and health care professionals alike would welcome improvements in ostomy devices to better meet such demands.

SUMMARY

The present disclosure provides aspects of a complementary-material element configured to be attachable to a base plate of an ostomy appliance. The complementary-material element is defined and characterized by the appended claims. Further disclosed is a kit of parts including a complementary-material element, a base plate and a collecting bag of an ostomy appliance.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1 further illustrates a kit of parts of the disclosure.

FIG. 3 is a cross-sectional view of one embodiment of a complementary-material element.

FIG. 4A is a cross-sectional view of one embodiment of a complementary-material element.

FIG. 4B is a cross-sectional view of the complementary-material element of FIG. 4A.

FIG. 5A is a perspective view of one embodiment of a complementary-material element.

FIG. 5B is a cross-sectional view of the complementary-material element of FIG. 5A.

FIG. 6 is a cross-sectional view of one embodiment of a complementary-material element.

FIG. 7A is a perspective view of one embodiment of a complementary-material element including a first entity and a second entity.

FIG. 7B is a cross-sectional view of the embodiment of the complementary-material element of FIG. 7A.

FIG. 8 is a cross-sectional view of a complementary-material element attached to a base plate of an ostomy appliance.

DETAILED DESCRIPTION

Figure 1:
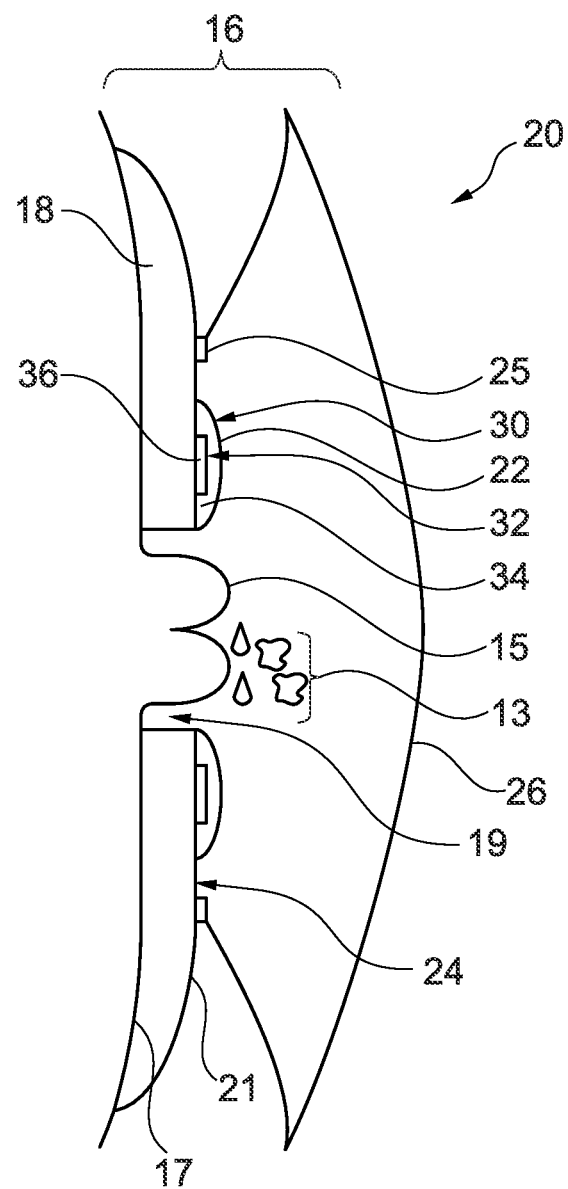
FIG. 1 is a cross-sectional side view of one embodiment of an ostomy appliance including a complementary-material element.

In the following Detailed Description, reference is made to the accompanying drawings, which form a part hereof, and in which is shown by way of illustration specific embodiments in which the invention may be practiced. In this regard, directional terminology, such as "top", "bottom", "front", "back", "leading", "trailing" etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably.

By (stomal) output is herein meant the effluent from a stoma, being faeces and/or urine in a more or less viscous form and/or mucins secreted from the epithelial layer of the alimentary canal. In the case of a colostomy, the output may be quite solid, whereas an ileostomy may produce more liquid output. The output may contain digestive fluids with enzymes and other components that may be aggressive to the skin and thus may cause damage and contact dermatitis of the skin in addition to maceration if brought into contact with it, as well as the output may comprise components that may attack and degrade the adhesive.

A person having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user. To some extent the 'generally perpendicular direction of the stoma' may be perceived more as an ideal rather than real direction, since many factors and dynamics continuously influence a stoma's condition.

The radial direction is defined as transverse to the axial direction that is transversely to the direction of the stoma. In some sentences, the words "inner" and "outer" may be used. These qualifiers should generally be perceived with reference to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the phrase "substantially" as a qualifier to certain features or effects in this disclosure is intended to simply mean that any deviations are within tolerances that would normally be expected by the skilled person in the relevant field.

In one aspect, the present disclosure relates to a complementary-material element which is configured to be attachable to a base plate of an ostomy appliance and comprising at least a first entity and a second entity, the first entity comprising a first material composition and the second entity comprising a second material composition different from the first material composition, wherein the second material composition comprises a neutralizing component configured to be releasable from the complementary-material element in response to subjection of the complementary-material element to moisture.

The complementary-material element (in the following also/interchangeably designated 'CME') is to be understood as an element which is separate from and attachable to a base plate of an ostomy appliance. The wording 'base plate' is commonly used within the technical field of ostomy appliances and the skilled person is familiar with this term. The term 'base plate' is used for that element or part of an ostomy appliance which attaches the appliance to a skin surface around a user's stoma, most commonly by an adhesive interface. Thus, it is the intention of the terminology 'CME' used in this disclosure to mean an element which is not itself a base plate of an ostomy appliance, but which is a 'stand-alone' element.

The 'CME' is configured to be attached to a base plate of an ostomy appliance, but is otherwise an individual, or distinct, element.

The 'CME' includes material which comprises at least a first material composition and a second material composition. The second material composition is different from the first material composition. Although one or more constituents (or the amount thereof) of the first and the second material compositions can be identical (be 'the same'), the 'total' second material composition is not identical to the 'total' first material composition. Providing the different first and second material compositions allows the 'CME' to have more than one effect and/or function to mitigate or solve more than one purpose in relation to an ostomy and/or ostomy appliance. One non-limiting example could be to both address absorption and counteracting of the damaging contents of stomal output.

Particularly, the second material composition of the 'CME' includes a neutralizing component. The neutralizing component is configured to be released from the 'CME' in response to subjection of the 'CME' to moisture. Thus, when the 'CME' is attached to (used with) a base plate of an ostomy appliance being worn by a user around a stoma exuding stomal output, the moisture content of the stomal output acts to initiate, sustain and/or accelerate release of the neutralizing component from the 'CME'. Suitable materials for the neutralizing component are discussed below.

According to the disclosure, the first material composition is comprised in a first entity of the 'CME', and the second material composition is comprised in a second, different entity of the 'CME'. By 'first' and 'second' entity it is to be understood that the first material composition is provided in a first structure (entity') of the 'CME' and the second material composition is provided in a second structure (entity') of the 'CME'. The first entity and the second entity should be understood as a first and second unit, element or part of the 'CME'. The first and the second material compositions are not mixed or blended to form a shared (or common) material matrix. Instead, the first entity and the second entity are to be understood to provide for the first material composition and the second material composition to be located structurally separate (apart) from each other in each their individual unit, element or part of the 'CME'. Various embodiments of the 'CME' including different implementations of the first entity and the second entity are discussed below.

When an ostomy appliance is applied to the skin surrounding a stoma, adhesive on the base plate ideally provides a tight fit or sealing to the skin, to avoid stomal output from propagating under the adhesive of the base plate, which is potentially damaging to the skin and prone to degrading the adhesive as explained above. Any stomal output propagating or seeping under the adhesive of base plate is to be avoided as best as possible because contents of such output can lead to damage to the skin and degradation of the adhesive, potentially resulting in adhesive failure and eventually leakage of the stomal output onto the user's clothes, presenting a stigmatising embarrassment and clearly discomfort to the user. However, experience has shown that avoiding any or all kind of such problems is extremely difficult and that users regularly are faced with these issues.

According the disclosure, such adhesive failures and other problems can be overcome in that the neutralizing composition included in the second entity of the 'CME' is configured to be released in the presence of moisture and thereby act to neutralize the aggressive contents of the stomal output to help avoid or reduce damage to the skin and/or degradation of the adhesive. Additionally, and/or alternatively, the neutralizer or neutralizing composition acts to slow or decelerate the damaging effects of the stomal output, in some cases providing for increased or prolonged wear time of the ostomy appliance, which in turn provides both practical and economic advantages.

When preparing a base plate of an ostomy appliance to fit an individual user's stoma and body (skin surface), it often involves trimming or cutting (e.g. with special scissors) into correct shape and size an ostomy receiving opening in the base plate of the appliance. To avoid the thereby cut edge from gnawing on the stoma, and since adaptation of such opening in the base plate is difficult to make with a great deal of precision, the cutting/adaptation almost always leaves a small gap (distance) between an edge of the cut opening in the adhesive base plate and the user's stoma, when the appliance is applied around the stoma of the user. However, such gap does help to provide room for the stoma to 'work' (i.e. expand and contract), caused inter alia by peristaltic movements of the intestine; often, the stoma enlarges when delivering stomal output and shortens when not. This gap is also called the peristomal gap. Stomal output inevitably flows into the peristomal gap and will over time be able to propagate under the adhesive interface between the skin and the base plate from the peristomal gap. Consequently, the necessary provision of an ostomy receiving opening and/or the peristomal gap also contributes to the risk of damage and degradation of the adhesive layer of the base plate followed potentially by skin damage, irritation, maceration and/or other skin problems.

By providing a 'CME' including a second entity with a neutralizer or neutralizing component together with a base plate for an ostomy appliance, the 'CME' provides for the neutralizing component to be directed into contact with the stomal output and into the peristomal gap. Both the user's skin and the adhesive layer on the base plate at, and adjacent to the peristomal gap, will thereby be protected from the damaging effects of the stomal output by the released neutralizer. While a small amount of neutralizing component may be forced or displaced into the collecting bag when stomal output exudes from (leaves) the stoma and passes through the stoma-receiving opening and into the collecting bag, the 'CME' of this disclosure is configured to ensure that a major portion of the neutralizing component is directed to flow particularly into the peristomal gap to interact with stomal output to neutralize its harmful components and avoid or delay degradation of the adhesive layer of the base plate.

Experience shows that stomal output can flow substantially continuously or enter the collecting bag in bursts when exiting the stoma, depending among other factors on the type of stoma. If a user of an ostomy appliance is in an upright position, stomal output may flow continuously downwards due to gravity and thereby act to primarily 'wet' or 'soil' a portion of the base plate located below (beneath or under) the stoma when the appliance is worn. However, stomal output can also creep upwards to 'wet' or 'soil' a portion of the base plate located above (higher or over) the stoma when the appliance is worn.

Particularly, when stomal output enters the inside of a collecting bag in bursts, with a distal wall of the collecting bag being pressed close to the stoma (e.g. due to the user's clothing, belt, trouser lining etc.), the stomal output is known to be able to spread all over a central portion of the base plate, including also the area above (higher than/over) the stoma. For a user wearing a collecting bag with his/her clothes pushing the collecting bag's distal wall against the stoma, stomal output can be trapped in and fill a volume defined by: the base plate, the distal wall of the collecting bag and an attachment between the base plate and the collecting bag (potentially a coupling arrangement between the base plate and the collecting bag). Thus, stomal output may not immediately or exclusively be forced downwards by gravity, but can also be affected (by force(s) acting on it) to 'wet' or 'soil' an area of the collecting bag above (over) an inlet opening in the collecting bag and possibly also 'soil' the peristomal gap.

In conclusion, during normal use of an ostomy appliance, stomal output does not subject itself to an 'idealistic behaviour' of simply being forced by gravity to the 'bottom' of the collecting bag's reservoir volume. Instead, stomal output can (or be forced to) travel in any direction from the inlet opening of the collecting bag, including to areas/locations above (higher/over) the stoma. In some cases, stomal output can even be smeared against the walls (distal and/or proximal) of the collecting bag and further onto anywhere on a distal surface of the base plate and 'back' into the peristomal gap. Consequently, it is not easy to foresee exactly where and how fast stomal output will 'end up' and present a problem. The present disclosure provides solutions which help avoid or prevent adhesive failure or at least reduce the impact of the stomal output's potentially damaging and detrimental effects on the user's skin surface, stoma and/or on the components of the ostomy appliance by offering a 'CME' which is configured to release a 'mitigating' neutralizer or neutralizing component.

From the above, it is understood that in conceiving the invention of the present disclosure, the inventors realized that the neutralizing component must not per se be provided close to, or in direct contact with, the stoma's surface, or directly onto the peristomal gap or skin surface for the neutralizing component to be able to provide its beneficial effects. Indeed, it was realized that the neutralizer's effects are achievable inter alia by allowing the neutralizing component to be released at or into the peristomal gap; into an area of the collecting bag around the bag's inlet opening, and/or on the base plate, such as on a central portion of the base plate, including on a distal surface of the base plate facing away from the skin of the user, when the ostomy appliance is worn. In some implementations, the 'CME' can be adapted to release the neutralizing component in more than one direction, such as towards a proximal surface of the base plate (facing the user's skin) and a distal surface of the base plate (facing or being exposed to the inside of the collecting volume of the collecting bag).

In embodiments, the 'CME' comprises an opening which is configured to receive the stoma and/or the stomal output from the user.

In embodiments, the second material composition can include more than one neutralizing component. In embodiments, a neutralizing component can include more than one kind of neutralizer (e.g. directed towards neutralizing different contents of the stomal output). In some implementations, the helpful effect(s) presented by one neutralizing component and/or one neutralizer can be amplified by the presence of another kind of neutralizing component and/or neutralizer to provide even better results in terms of preventing or at least reducing the prevalence of adhesive failures, skin maceration, leakage incidents etc. This in turn helps provide for longer wear time of the ostomy appliance.

In embodiments, one or both of the first material composition and the second material composition is/are provided in a matrix structure.

In embodiments, a matrix structure (Matrix') of the second material composition comprises a neutralizer incorporated therein. The neutralizer can be dissolved in the matrix or it can be dispersed as particles in the matrix. In embodiments, the matrix comprises coated neutralizing substance particles. The matrix serves as a carrier of the neutralizer and is configured to release the neutralizer.

In embodiments, the matrix is configured to release the neutralizer when the matrix is subjected or exposed to certain conditions. Such conditions may for example be in the presence of stomal output containing moisture or in the presence of moisture from other sources, e.g. sweat from the user's body.

Inside the collecting volume of a collecting bag, humidity will quickly reach close to 100% humidity, so the presence of moisture is substantial. In embodiments, the release of neutralizer initiates shortly after applying the ostomy appliance on the user, due to the high relative humidity in the collecting bag.

In embodiments, the matrix comprises one or more of a gel, foam, film layer or paper or a coating. Such coating may for example be solid or powder coating. In embodiments, the matrix and the neutralizer form a colloidal solution such as a sol. One suitable example of a matrix comprises an adhesive comprising 50% w/w polyisobutylene (PIB) and 25% w/w CMC and 25% w/w pectin.

In embodiments, a matrix in the form of a water-soluble film comprises a PVOH based thermoplastic film, such as a Monosol® 7031 film from kurakay WS Film Division™, Portage, Ind., United States.

In embodiments, the matrix is configured to be soluble in water (moisture) or a component of the stomal output. It can be slowly soluble, by slowly is herein meant that the matrix will not degrade instantly, but slowly dissolve during wear of the base plate.

In embodiments, the matrix is configured to absorb moisture and turn into a gel like material when wetted by moisture uptake. The gel can be delivered in an initial dry form, and configured to subsequently swell into a gel when brought into contact with moisture. The gel can be slowly soluble in water or in a component of the output (moisture) or it can be insoluble, but able to release the neutralizer when exposed to the stomal output and/or moisture. Examples of suitable materials for the matrix may be polyethylene glycol (PEG), polyvinyl alcohol (PVA), polyvinyl pyrrolidone (PVP), ethylene vinyl acetate (EVA) based matrix and hydrocolloids such as CMC or gelatine.

In embodiments, the matrix comprises polysaccharides and/or hydrocolloids. The polysaccharides or hydrocolloids can be configured to dissolve or hydrate when exposed to output, thereby releasing the neutralizer.

In embodiments, the matrix comprises protein.

In embodiments, the matrix is substantially non-adhesive. By non-adhesive is to be understood that the matrix is not adhesive (does not stick). A non-adhesive matrix will be less prone to sticking to the distal wall of the bag. In some implementations, however, the matrix is configured to, under certain circumstances, become slightly sticky when wetted In embodiments, one or both of the first entity and the second entity of the complementary-material element is/are configured to be attached to the other entity (respective first or second entity) and/or a base plate of an ostomy appliance. In embodiments, the first entity and/or the second entity comprise(s) attachment means for attaching to the other entity. In embodiments, wherein attachment means are provided on both entities, the attachment means on a respective entity is/are configured to engage with the attachment means on the other entity. In embodiments, the attachment means can comprise mutually corresponding attachment means (i.e. configured to interfit with each other).

In embodiments, the first entity is configured to form a centre portion and a peripheral portion of the complementary-element, wherein the centre portion comprises one or more grooves. In embodiments, the second entity comprises one or more tongues. In embodiments, the one or more tongues of the second entity is/are configured to combine with the one or more grooves of the first entity. In embodiments, the combination of the one or more tongues of the second entity with the one or more grooves of the first entity, provides for the second material composition to leak through the edge formed by the first entity and into the peristomal gap. In some implementations, the first entity can thereby be seen to hold or act as a reservoir portion for the second material composition, while also allowing the second material composition to be guided adequately to the peristomal gap. Moreover, the combination of the one or more tongues of the second entity with the one or more grooves of the first entity, also serves to provide mutually corresponding attachment means between the first entity and the second entity.

Thereby, the first entity and the second entity are attachable to each other by a user or a health care professional. Alternatively, the first and the second entity are attached to each other at manufacture and delivered to the user in attached configuration.

In embodiments, the attachment means comprise(s) adhesive attachment means, such as, but not limited to, including an adhesive surface on at least the first or the second entity configured to glue or stick to a counterpart surface on the other entity or on the base plate.

In embodiments, the attachment means comprise(s) mechanical attachment means, such as, but not limited to, including hook and loop type connections (incl. Velcro®), press studs or by press fitting the first and the second entities into engagement with each other. In embodiments, more than one type of attachment means is provided on the first entity and the second entity.

In embodiments, the attachment means are configured such that the first and second entities attach and combine in an inter-fitting relationship, such as to provide at least one smooth major external surface of the complementary-material element.

In embodiments, the 'CME' further comprises an adhesive material element. In embodiments, the adhesive material element is attached to or located on an external surface of the first entity. In embodiments, the adhesive material element is attached to or located on an external surface of the second entity. In embodiments, the adhesive material element is attached to or located between the first entity and the second entity. In some implementations, the adhesive material element is useful in helping to secure the 'CME' to the peristomal skin surface of the user. Further, in embodiments, the adhesive material element can help secure the ostomy appliance to the skin surface of the user in combination with the adhesive on the base plate.

In embodiments, the adhesive material element is comprised in the first entity of the complementary-material element. In embodiments, the first material composition of the first entity comprises an adhesive material. In embodiments, the first material composition of the first entity consists of at least one adhesive material. Some examples of suitable paste material types can be found in applicant's publications WO2010/069334 and WO98/17329.

In embodiments, the adhesive material element is comprised in the second entity of the complementary-material element. In embodiments, the second material composition of the second entity comprises an adhesive material. In embodiments, the second material composition of the second entity consists of at least one adhesive material and a neutralizer. In embodiments, the second material composition comprises a moldable or pliable material. This provides for the second material composition to be further adaptable and/or customizable in the peristomal area. In embodiments, the moldable or pliable material is an adhesive material.

In embodiments, the adhesive material element is provided as an adhesive layer on an external surface of the first entity. The adhesive layer can be sprayed or coated onto the external surface of the first entity. In embodiments, the adhesive layer can be provided in a thickness of approximately 50 μm-2000 μm, such as 100 μm-300 μm.

In embodiments, the adhesive material element includes at least one definite zone of adhesive material. Thereby, it is to be understood that the adhesive material can be provided in one or more discrete areas of a finite extent. In one embodiment, the at least one definite zone of adhesive material is provided on an entirety of an external surface of the first entity facing away from the second entity. In embodiments, the adhesive material is provided in a plurality of individual (discrete) areas. In embodiments, the plurality of individual areas is arranged to form a "polka-dot-like" pattern. The "polka-dot-like" pattern can be provided as a structured or random distribution of the "dots". In embodiments, the plurality of individual areas is provided on an external surface of the first entity. In embodiments, each area of the plurality of individual areas is sprayed or coated onto an external surface of the first entity.

In embodiments, an intermediate film material is provided between the adhesive material element and one or both of the first entity and the second entity. Thereby, it can be ensured that the adhesive material of the adhesive material element is separated and/or protected from the first material composition of the first entity and/or from the second material composition of the second entity. Particularly, the intermediate film material can help to protect the adhesive material element from moisture from the stomal output, especially during release of the neutralizing component from the second material composition of the second entity. In embodiments, wherein the second material composition comprises a mouldable material, the application of an intermediate film can be particularly advantageous. In embodiments, this provides for preventing migration of volatile components of the mouldable second material composition into the other elements of the ostomy appliance, such as the bare plate adhesive.

In embodiments, the first entity and the second entity are arranged in a side-by-side relationship with each other. This should be interpreted such that if one imagines the 'CME' to be laid down on a flat surface, the first entity and the second entity only touch each other at their outer peripheries and are not in a layered nor partly overlapping configuration. In embodiments, the first entity and the second entity are arranged side-by-side along a portion of their periphery.

In embodiments, the second entity is surrounded by the first entity. This should be interpreted such that the second entity is of a finite three-dimensional structure. In particular, in embodiments wherein the first and second entities are of limited 'height' (axial extent 'away from the skin surface' when seen in relation to being located on a user's body), all locations on an outer periphery of the second entity is engaged with, or at least all face towards, locations on an inner periphery of the first entity. In embodiments, the complementary-material element is configured to be provided to a user such that the first entity at least partially enclosed the second entity. Thus, in some embodiments, the second entity is at least partially contained in a portion of the first entity. In one embodiment, the second entity is configured to initially be completely contained inside the first entity (i.e. when taken in use).

In embodiments, the first material composition and the second material composition are provided as a plurality of alternating zones of material. In embodiments, the plurality of alternating zones can be understood as corresponding to a plurality of individual entities. i.e. first, second, third, fourth, fifth etc. individual entities. In embodiments, each individual entity of the plurality of entities comprise a different material composition, i.e. each material composition of an entity is different from the material compositions comprised in other entities. In other embodiments, one or more of the individual entities comprise(s) identical material compositions. One non-limiting example could be a 'CME' comprising six zones of material alternating between a first material composition and a second material composition, i.e. such that e.g. a first, a third and a fifth entity or zone comprises a first material composition and a second, fourth and sixth entity or zone comprises a second material composition.

In embodiments, one or more zones of material or entities can be entirely surrounded at all edges by one or more other zones of material or entities. In embodiments, one zone of material or entity can be understood to form an 'island' in the other zone of material or entity, or a plurality of zones of one material can form a plurality of such 'islands' in the second material.

In embodiments of the 'CME', two or more entities comprising at least two different material compositions are spirally wound together to form (two or more) neighbouring zones of material each provided substantially in the shape of an Archimedean spiral which can be more or less deformed (i.e. may not form a completely 'perfect' spiral). Such embodiments of the 'CME' can be produced by stacking sheets or lengths of the desired materials, rolling the stack as a person would roll a carpet and slicing the roll thus formed substantially perpendicularly to its axis. These embodiments of the 'CME' are particularly production friendly, as discussed with regard to base plates of an ostomy appliance in applicant's published application WO 89/05619.

In embodiments, the 'CME' comprises at least a first entity comprising a first material composition and a second entity comprising a second material composition formed in the shape of an Archimedean spiral. In embodiments, the first material composition comprises a paste material and the second material composition comprises a neutralizer component. In embodiments, the first material composition consists of a paste material and the second material composition consists of a neutralizer.

In embodiments, the 'CME' comprises a first entity comprising a first material composition, such as, but not limited to, a paste material, and a second entity comprising a second material composition, the second material composition comprising at least two different neutralizers or neutralizing components, wherein the at least two different neutralizers are provided in zones formed in the shape of an Archimedean spiral. Particularly, in embodiments, the first entity is provided in a layered configuration with the second entity comprising the Archimedean spiral of two different neutralizers.

In embodiments, the second entity forms a centre portion of the 'CME' and the first entity forms a peripheral portion of the 'CME'. These embodiments are particularly, but not exclusively, suitable for quick release of the neutralizer from the second material composition of the second entity and to be directed into the peristomal gap to neutralize stomal output.

In embodiments, the first entity and the second entity are configured in a layered relationship, such that one entity is on top of the other entity. In one embodiment configured with the first and second entities in a layered relationship, the first material composition of the first entity in configured to be durable (i.e. not easily erodible by stomal output), and the second material composition is configured to be relatively easily erodible and to release the neutralizer component. Thereby, these embodiments provided for the 'CME' to be both durable and to provide protection for the peristomal gap and peristomal skin surface, and work to quickly neutralize stomal output.

In embodiments, the second entity of the 'CME' comprising a second material composition comprising a neutralizer is configured to be un-foldable from an initial configuration. In other words, in these embodiments the second entity is provided as a folded entity when received by the user. In embodiments, the second entity is folded to form a substantially circular or annular ring of the second material composition. In embodiments, the ring of the second material composition of the second entity is provided in a layered relationship with the first entity. In embodiments, the initially folded second entity is provided as a ring around a preformed ostomy-receiving opening of, and on one surface of, the first entity. In these embodiments, the first entity has a greater radial extent or larger outer diameter than the second entity. By providing the second entity as an (un) foldable ring, the user or HCP can help to customize how the second material composition of the second entity is distributed in relation to the ostomy appliance and thus, for example, help direct an additional or a major portion of the neutralizing component into the peristomal gap or close to the peristomal skin surface. Particularly, but not exclusively, the user may initially locate the 'CME' around his/her stoma, possibly guiding the stoma through the preformed ostomy-receiving opening. Subsequently, a base plate of an ostomy appliance can be applied "on top" of the 'CME' around the stoma and adhered to the skin surface. Then, the user can unfold the annular ring of the second material composition, such that the complementary material ring is 'flipped' or 'bent' over radially, and onto a distal surface of the base plate, to thereby cover or to enter into the peristomal gap, thus providing protection of the base plate adhesive and the peristomal gap from the stomal output.

In embodiments, the 'CME' comprises a plurality of entities provided as individual layers provided alternatingly on top of each other. In embodiments, each one of the plurality of individual layers is formed having identical or substantially identical diameters with the other individual layers. In embodiments, each individual layer can comprise a material composition which is different from the material compositions of the other individual layers.

In embodiments, the plurality of layers alternate between a first entity comprising a first material composition comprising a material suitable for moisture transportation and a second entity comprising a second material composition comprising a neutralizer. The material suitable for moisture transportation can be understood to form a wick or wicking element. In embodiments, one or more through-going 'tunnel' holes is/are provided in the axial direction through the individual layers. Thereby, these embodiments provide for the possibility that stomal output not only can wet or moisten the neutralizing component at the outer edge of the layers, but can also 'penetrate' into the layers through the one or more additional 'tunnel' holes. In embodiments, wherein more than one or a plurality of 'tunnel' holes are provided, these can advantageously be arranged in a symmetrical pattern and distributed around an ostomy-receiving opening. This can provide for faster and/or substantially more release of neutralizer from the second material component, because moisture from the stomal output can engage with the second material composition at a plurality of locations. Thereby, a larger amount of neutralizer can be 'activated' quicker. These embodiments also further add to the options for customizing the 'CME' to the needs of the individual user.

In embodiments, the wick or wicking element can help to direct excess stomal output faster away from the peristomal gap. In this manner, the wick or wicking element further forms a physical 'barrier' or means in addition to the chemical means of the neutralizer component. In embodiments, the wick material includes cotton, such as a string of braided cotton, gauze, hydrophilic sponge, fabric, paper or other. In embodiments, the wick or wicking element can be made from any suitable material for the purpose, such as an absorbent material that is capable of transporting the liquid from one location to another location. The wick material can be of a kind which absorbs and transports the liquid using capillary action, wherein the structure and the choice of wick material ensures that the liquid is absorbed into the wick material.

To further help understanding the distinguishing between the different embodiments defining individual ways of providing the first entity and the second entity in relation to each other, one can think of the "side-by-side" relationship in relation to looking at a horizontal plane through a cross-section of the 'CME', and the "on top of each other" relationship in relation to looking at a lateral plane through a cross-section of the 'CME'.

In embodiments, the first material composition and/or the second material composition comprise(s) a material which is configured to gel in contact with moisture. In embodiments, the material which is configured to gel includes gelatine. In embodiments, at least the second material composition comprises a material which is configured to gel in contact with moisture. Such gelling effect can be configured to be relatively pronounced and thereby work to increase a volume of the gelling material substantially and create a 'bulk' of gelled material. These embodiments are particularly, but not exclusively, suitable for providing a 'CME' which offers both a physical blocking of stomal output—created by the 'bulk' of gelled material—and a chemical blocking—created by the neutralizer being released from the second material composition. In embodiments, the first entity and/or the second entity can be configured to provide for the gellable material to create a 'turtle necking' effect of the material around the stoma when the material gels from the moisture uptake, thereby providing the gelled mass as a physical barrier against stomal output. In embodiments, one or more further absorbent material(s) is selected from the group consisting of hydrocolloid, starch, water soluble salt, mono, di- and oligosaccharides, sugar alcohols, polypeptides, organic acids, inorganic acids, amino acids, amines, urea, super absorbent particles such as polyacrylic acid, glycols such as polyethylene glycol, fumed silica, xanthan gum and bentone. In embodiments, the PAA is crosslinked PAA. In embodiments, the PAA is partially neutralized PAA. In embodiments, the PAA is Carbopol 974P NF Polymer from Lubrizol Advanced Material, Inc. In embodiments, the PAA has a carboxylic acid content in the range 56-68%.

In embodiments, the second material composition is at least located next to the ostomy receiving opening in the base plate. This helps enable the neutralizer to enter the peristomal gap when released from the second material composition. By next to the ostomy receiving opening is to be understood that the second material composition defines at least a portion of an inner periphery or rim of the ostomy receiving opening.

In embodiments, the first material composition of the 'CME' is a paste. Some examples of suitable paste material types can be found in applicant's publications WO2010/069334 and WO98/17329. In embodiments, the paste material is provided by the first entity and forms a more durable element of the 'CME' suitable for carrying the second entity with the second material composition comprising the neutralizer to be released.

In embodiments, the 'CME' comprises at least one release liner. Thereby, the 'CME' can be more easily handled separately from a base plate of an ostomy appliance with which the 'CME' is to be used. Particularly, in embodiments wherein the first entity and/or the second entity includes an adhesive material element, the release liner is useful. In embodiments, the 'CME' comprises at least one release liner which covers at least one surface of the first entity. In other embodiments, one release liner can be configured to cover more than one surface, or portion of an external surface, of the first entity. In yet other embodiments, the 'CME' comprises at least one release liner which covers at least one surface of the second entity. In other embodiments, one release liner can be configured to cover more than one surface, or portion of an external surface, of the second entity. In embodiments, one release liner covers an entirety of an external surface of the 'CME', i.e. an external surface formed in combination by the first and the second entities. In embodiments, the 'CME' is entirely contained within ('wrapped' in) one release liner. In other embodiments, the first entity and the second entity are provided in a layered configuration and an ostomy-receiving opening is provided through entities of the 'CME', in which case the release liner is configured not to cover the inner periphery of the first and second entities at the ostomy-receiving opening.

In embodiments, the 'CME' includes a separation element between the first material composition and the second material composition. In embodiments, the 'CME' includes a separation element between the first entity and the second entity. In embodiments, the 'CME' comprises at least one separation element which covers at least one surface of the first entity. In other embodiments, one separation element can be configured to cover more than one surface, or portion of an external surface, of the first entity. In yet other embodiments, the 'CME' includes at least one separation element which covers at least one surface of the second entity. In embodiments, one separation element can be configured to cover more than one surface, or portion of an external surface, of the second entity. In embodiments, one separation element covers an entirety of an external surface of the 'CME', i.e. an external surface formed in combination by the first and the second entities.

In embodiments, the first entity and the second entity are provided in a layered configuration including a separation element provided in the layered configuration between the first and second entities. In embodiments, an ostomy-receiving opening is provided through the layers. In embodiments, the separation element includes an elastic material, such as an elastic carrier foil for separating the first material composition and the second material composition from each other. In embodiments, the separation element includes a tape or tape-like material.

In one aspect, the disclosure relates to a kit of parts comprising a complementary-material element as disclosed herein and a base plate for an ostomy appliance. The base plate comprises an adhesive provided on a first surface of a carrier film. The second surface of the carrier film is formed by the carrier film itself. Optionally, the base plate comprises a release liner provided on the adhesive first surface of the carrier film.

In embodiments, the first entity and/or the second entity of the complementary-material element is/are attachable to the base plate by a user or a health care professional. Alternatively, the first and the second entity are attached to each other and/or to the base plate at manufacture and delivered to the user in an attached configuration. Such attachment inter alia allows for easier adaptation of a stoma-receiving opening in the base plate when customization of the size and shape of the opening to the user's stoma is required.

In embodiments, the kit of parts further comprises a body waste collecting bag attached to the second surface of the carrier film of the base plate. In these embodiments, the collecting bag is already attached to the base plate at manufacture and may be understood as a one-piece ostomy appliance, as is commonly understood in the ostomy appliance area. Such embodiments of a one-piece ostomy appliance of the disclosure provide one-piece appliances which may have prolonged wear time, due to the combination with the attached or attachable complementary-material element. The collecting bag can thus be detachably or permanently attachable to the base plate via a coupling arrangement.

In embodiments, a first coupling half is provided on the second surface of the carrier film of the base plate. The body waste collecting bag includes a second coupling half provided around an inlet opening of the collecting bag. This provides for the complementary-material element of the disclosure to also be used with and improve the life- or wear time also of a two-piece ostomy appliance, also commonly understood in the area.

In embodiments, the base plate comprises second attachment means for attachment to the complementary-material element. In these embodiments, the first entity and/or the second entity comprise(s) first attachment means to engage or attach to the second attachment means of the base plate.

In embodiments, the complementary-material element is configured as a ring-shaped element or as a disc-shaped element. Thereby, the 'CME' is intuitive and easily handled by the user or health care professional. This is particularly, but not exclusively, advantageous when the 'CME' is combined with and attached to a base plate of an ostomy appliance by the user or health care professional (i.e. it is not attached to the base plate at manufacture) before being applied to the skin of the user.

In embodiments, the 'CME' comprises an opening which is configured to receive the stoma and/or the stomal output from the user. In some implementations, the 'CME' is a ring-shaped element comprising a central opening, wherein attachment of the 'CME' to the base plate becomes particularly intuitive, because the ring-shaped element (the 'CME') is configured to align with a stoma-receiving opening in the base plate and to be customized to fit well with the size and shape of an individual stoma.

In embodiments, the collecting bag comprises a second half of a coupling interface that is configured to couple with a first half of the coupling interface on the base plate to attach the stomal collecting bag to the base plate.

In embodiments, a distal surface of the base plate includes a first half of a coupling interface for coupling the base plate to a collecting bag. In one embodiment, the coupling half is a flange adapted to provide a surface for attaching another coupling half in the form of an adhesive flange provided on the collecting bag. In embodiments, the first half of the coupling interface is configured as a flexible, planar annular flange optionally comprising an adhesive. The first coupling half is adapted to couple with a second coupling half provided around an inlet opening of the collecting bag by means of an adhesive. The adhesive coupling may provide a releasable or a permanent adhesive coupling engagement between the components.

In embodiments, the coupling half is an annular ring comprising an upstanding flange protruding from the distal surface perpendicular thereto for attaching another coupling half in the form of a coupling ring provided on the collecting bag. In one embodiment, a first coupling half is attached to a distal surface of the base plate. In embodiments, the first coupling half is attached to the distal surface by an adhesive or by welding, but other ways of attaching are acceptable. Other types of suitable coupling arrangements are widely available within the ostomy care field.

In embodiments, the kit of parts includes a packaging configured to contain at least one complementary-material element, at least one base plate for an ostomy appliance and at least one collecting bag adapted to attached to the base plate. The complementary-material element is attachable to the base plate as described in this disclosure. In embodiments, the kit of parts includes a set of instructions for use of the combination of the components of the kit of parts, and particularly with instruction on how to apply and use the complementary-material element in combination with the base plate and the collecting bag.

The neutralizer (neutralizing component)

By neutralizer (neutralizing component) is herein meant a neutralizing substance capable of neutralizing or at least minimizing the level of skin- or adhesive-aggressiveness of stomal output.

In embodiments, the neutralizer comprises a clay, such as organophilic clay, for example bentonite or synthetic clay such as laponite. Examples of such clays are disclosed in EP 1 140 009.

In embodiments, the neutralizer comprises potato-derived inhibitors or protease inhibitors. Examples of potato-derived inhibitors such as potato protein are disclosed in EP 1 736 136.

In embodiments, the neutralizing component can include an adhesive. In other embodiments, the neutralizing component comprises a powder. In other embodiments, the neutralizing component comprises a liquid. In other embodiments, the neutralizing component comprises a gel. In other embodiments, the neutralizing component comprises a plurality of pellets. In yet other embodiments, the neutralizing component comprises a combination of any one or more of an adhesive, a powder, a liquid, a gel and/or a plurality of pellets. These options each provides one or more different advantages such as including, but not limited to, manipulability, shelf life, suitability for different kinds of stomal output (colostomy output tends to be much more solid than ileo- and urostomy output), processing characteristics during manufacture and others. By selectively applying these options, individually or in combination, to meet particular requirements of a target ostomy/ostomist group, the suitability of the ostomy appliance and the improvement in reduction or elimination of the problems discussed above, including reducing the risk of leakage, can be significantly improved.

Particularly, in embodiments wherein the neutralizing component comprises an adhesive, suitable materials include adhesives, such as, but not limited to, adhesive pastes. Suitable materials for a paste-type adhesive comprise adhesives of the types disclosed in WO2010/069334 and WO98/17329. Other types of adhesive pastes are also acceptable.

DETAILED DESCRIPTION OF THE DRAWINGS

FIG. 1 is a schematic cross-sectional side view of one embodiment of an ostomy appliance 20 including a complementary-material element 22, a base plate 24 to which the complementary-material element 22 is attached, and a stomal output collecting bag 26 coupled to the base plate at location 25 and configured to collect stomal output 13 coming out of the user's stoma 15. The base plate 24 is adhesively attached to the skin surface 17 surrounding the stoma 15. Also visible is an area or zone immediately surrounding the stoma 15, the area or zone designated the peristomal gap 19. The embodiment of FIG. 1 further illustrates a first entity 30 and a second, different entity 32 of the complementary-material element 22. The first entity 30 comprises a first material composition 34 and the second, different entity 32 comprises a second material composition 36. The second material composition 36 is different from the first material composition 34.

Figure 2B:
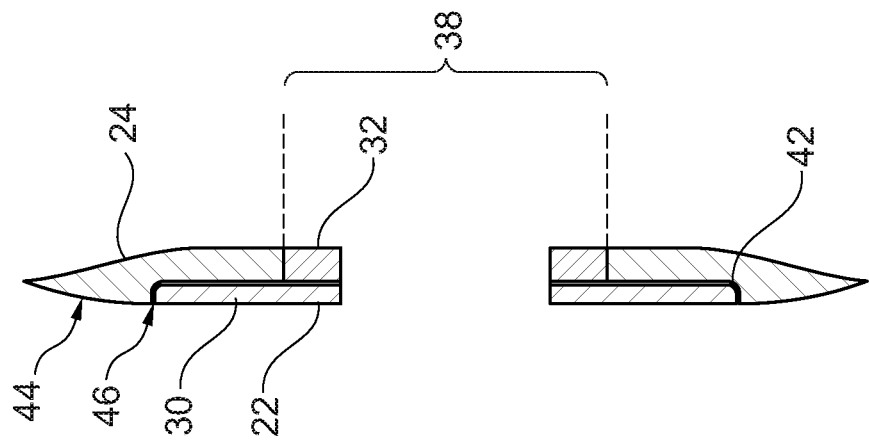
FIG. 2B is a cross-sectional side view of one embodiment of the complementary-material element combined with a base plate of an ostomy appliance wherein a complementary-material element is attached to the base plate.
Figure 2A:
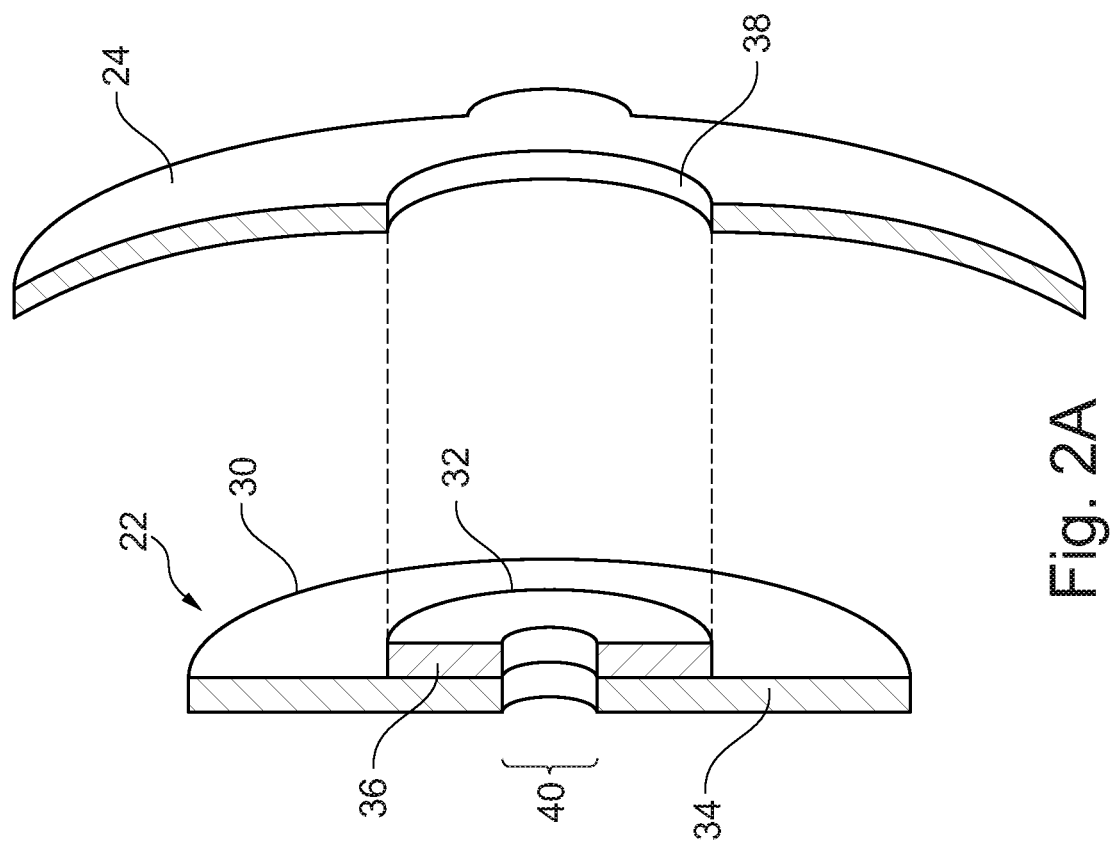
FIG. 2A is a part cross-sectional exploded view of one embodiment of a complementary-material element.

FIG. 2A is a schematic, part cross-sectional exploded view of one embodiment of a complementary-material element 22 and a base plate 24.

In the embodiment of FIG. 2A, the second entity 32 is located on a distal side of the first entity 30. In one embodiment, the first entity 30 and the second entity 32 are configured in a layered relationship, such that one is on top of the other.

FIG. 2B is a schematic, cross-sectional side view of the complementary-material element 22 and base plate 24 of FIG. 2A in a position wherein the complementary-material element 22 is attached to the base plate 24. FIG. 2B further illustrates one embodiment, wherein the complementary-material element 22 is configured to engage with the base plate 24 such that the second entity 32 extends at least partway through an opening 38 in the base plate 24. In embodiments, the opening 38 is configured to have a larger diameter than the diameter of a stoma-receiving opening 40 in the complementary-material element 22. In embodiments, the stoma-receiving opening 40 is of uniform diameter in the first entity 30 and the second entity 32 of the complementary-material element 22.

In embodiments, as illustrated by example in FIG. 2B, the base plate 24 is configured to include a recess portion 42 in which the first entity 30 of the complementary-material element 22 can be fitted. In embodiments, the dimensions of the recess 42 and of the first entity 30 are adapted to combine to have a proximal surface 44 of the combined complementary-material element 22 and base plate 24 including a non-offset transition 46 between the first entity 30 and the base plate 24.

FIG. 3 is a schematic, cross-sectional view of one embodiment of a complementary-material element 22 comprising a first entity 30 and a second entity 32. The second entity 32 is configured to provide a centre portion 48 of the complementary-material element 22 and the first entity 30 is configured to provide a peripheral portion 50 of the complementary-material element 22. In the embodiment illustrated in FIG. 3, the second entity 32 is located in a recess 52 of the first entity 30. Moreover, the illustrated embodiment of the second entity 32 in FIG. 3 comprises a flange portion 54 configured to fit in the recess 52 of the first entity 30 of the complementary-material element 22. The first entity 30 includes a first material composition 34 and the second entity 32 includes a second material composition 36, which is different from the first material composition 34 of the first entity 30. In the illustrated embodiment, a stoma-receiving opening 40 is provided in and extends through the second entity 32. The first entity 30 includes a central through-going opening 41 combining with the recess 52 to receive the second entity 32.

FIG. 4A is a schematic, cross-sectional view of one embodiment of a complementary-material element 22 comprising a first entity 30 and a second entity 32. In the embodiment of FIG. 4A, the first entity 30 is configured to form both a centre portion 48 and a peripheral portion 50 of the complementary-material element 22, except for the centre portion 48 being interrupted by one or more tongues 56 of a second entity 32 located in a recess 52 of the first entity 30, each tongue 56 extending radially inwardly from a primary portion 60 of the second entity 32. Moreover, the one or more tongues 56 is/are configured to fit in corresponding grooves 62 of the centre portion 48 of the first entity 30 of the complementary-material element 22. As in the embodiment of FIG. 3, the first entity 30 includes a first material composition 34 and the second entity 32 includes a second material composition 36, which is different from the first material composition 34. In the illustrated embodiment, a stoma-receiving opening 40 is provided by, and extends through, the centre portion 48 of the complementary-material element 22, formed by the first entity 30 and the one or more tongues 56 of the second entity 32.

FIG. 4B is a schematic, cross-sectional view of the complementary-material element 22 of FIG. 4A comprising the first entity 30 and the second entity 32 and attached to the proximal side of a base plate 24. The proximal side of the base plate 24 includes an adhesive 64 for attaching (adhering) the base plate 24 to the skin surface of the user around the stoma. In the embodiment of FIG. 4B, a primary portion 60 of the second entity 32 locates between the first entity 30 and a proximal surface of the base plate 24. Although not indicated in the cross-section of FIG. 4B, the one or more tongues 56 of the second entity 32 extend(s) to the stoma-receiving opening 40, further allowing for the second material composition 36 of the second entity 32 to be released into the opening 40 and start to engage with stomal output.

FIG. 5A is a schematic perspective view of one embodiment of a complementary-material element 22 comprising a first entity 30 and a second entity 32 provided in a layered relationship with each other. In the embodiments illustrated by FIGS. 5A-B, the second entity 32 is a second material composition comprising a neutralizer and the second entity 32 is configured to be un-foldable from the initial, folded configuration illustrated in FIG. 5A to the un-folded configuration illustrated in FIG. 5B. This is indicated by arrows R. The initially folded second entity 32 of FIG. 5A is provided as a ring 66 around a preformed ostomy-receiving opening 21 and on one surface of the first entity 30. By unfolding the ring 66, as indicated in FIG. 5B, the user or HCP can help to distribute the second material composition 36 of the second entity 32 containing the neutralizer to be released. In the example illustrated in FIG. 5B, the ring 66 is divided into two pieces to allow for additional customization to protect the base plate adhesive near the peristomal gap or close to the peristomal skin surface.

FIG. 6 is a schematic cross-sectional view of one embodiment of a complementary-material element 22 comprising a first entity 30 and a second entity 32. The complementary-material element 22 is shown attached to a base plate 24 of an ostomy appliance. The combined complementary-material element 22 and base plate 24 are shown mounted around a stoma 15 of a user. The second entity 32 comprises a neutralizer and is suitable for neutralizing stomal output exuding from the stoma 15 and entering into the peristomal gap 19.

FIG. 7A is a schematic, perspective view of one embodiment of a complementary-material element 22 including a first entity 30 and a second entity 32. The second entity 32 is provided entirely along an inner periphery of an ostomy-receiving opening 21 in the first entity 30 of the complementary-material element 22 and configures to form a ring or annular element 68. FIG. 7B is a schematic cross-sectional view of the embodiment of the complementary-material element 22 of FIG. 7A. The ring or annular element 68 forming the second entity 32 can be understood to be in a side-by-side relationship with the first entity 30. In the embodiment of FIG. 7B, the ring or annular element 68 comprises a curved external surface 70. Other shapes of the external surface of the ring or annular element 68 are acceptable.

FIG. 8 is a schematic cross-sectional view of a complementary-material element 22 attached to a base plate 24 of an ostomy appliance and located in the peristomal skin area around a stoma 15 between a proximal surface 70 of the base plate 24 and the user's skin surface. In the illustrated embodiment of FIG. 8, the first entity 30 and the second entity 32 are configured in a layered relationship, such that the second entity 32 is on top of the first entity 30. This is further illustrated in FIG. 8 by denoting the first entity 30 with letter 'A' and the second entity 32 with letter 'B'. In the embodiment of FIG. 8, the first material composition 34 of the first entity 30 is configured to be durable or particularly resistant against stomal output, and the second material composition 36 comprises the neutralizer component and is configured to be relatively easily erodible, which can help to promote the release of the neutralizer. The first entity 30 with the durable first material composition 34 is useful in physically protecting the adhesive 72 on the base plate 24 as well as the peristomal skin surface, and the second entity 32 with the erodible, neutralizer containing second material composition 36 is useful in chemically protecting these. Further, in embodiments, the first and/or second material compositions 34, 36 include a material suitable for creating a gelling effect, whereby the gelled material additionally functions to provide physical protection of the base plate adhesive 72 and the peristomal skin surface. In alternative embodiments, the first entity 30 and the second entity 32 are provided with 'A' on top of 'B' instead. These options add to the customization options when applying the complementary-material element 22 of the disclosure in combination with a base plate 24 of an ostomy appliance.

Figure 9:
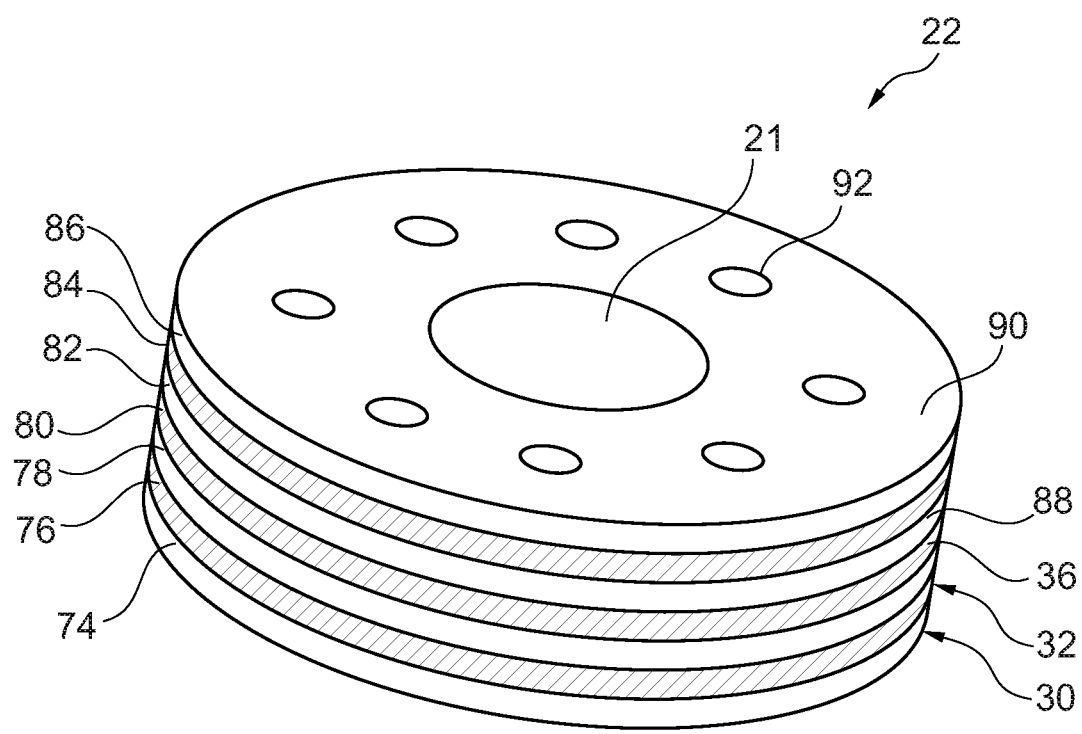
FIG. 9 is a perspective view of one embodiment of a complementary-material element including a plurality of entities.

FIG. 9 is a schematic perspective view of one embodiment of a complementary-material element 22 having a plurality of entities provided as individual layers 74, 76, 78, 80, 82, 84, 86 placed alternatingly on top of each other. In FIG. 9, each one of the plurality of individual layers 74, 76, 78, 80, 82, 84, 86 has the same diameter as the other individual layers. In FIG. 9, the plurality of layers 74, 76, 78, 80, 82, 84, 86 alternates between a number of first entities 30 comprising a material 88 suitable for moisture transportation and a number of second entities 32 comprising a second material composition 36 comprising a neutralizer. The material 88 suitable for moisture transportation can be understood to form a wick or wicking element 90. In the illustration of FIG. 9, a plurality of through-going 'tunnel' holes 92 are provided in an axial direction of the complementary-material element 22 through the individual layers 74, 76, 78, 80, 82, 84, 86. In FIG. 9, the plurality of 'tunnel' holes 92 are provided in a symmetrical pattern and distributed around an ostomy-receiving opening 21 of the complementary-material element 22. This provides for faster and/or substantially more release of neutralizer from the second material component 36, because moisture from the stomal output can engage with the second material composition 36 at a plurality of locations, including inside the 'tunnel' holes 92.

Figure 10A:
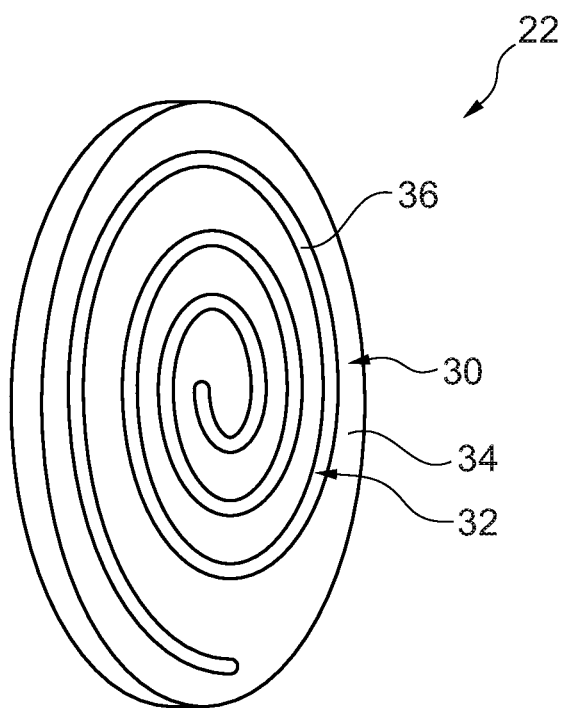
FIG. 10A is a perspective view of one embodiment of a complementary-material element including a first entity including a first material composition and a second entity including a second material composition.

FIG. 10A is a schematic perspective view of one embodiment of a complementary-material element 22 including a first entity 30 including a first material composition 34 and a second entity 32 including a second material composition 36 formed together in the shape of an Archimedean spiral. The embodiment of FIG. 10A is particularly useful for providing the possibility of distributing neutralizer released from the second material composition 36 not only at or near the peristomal area, but indeed over a larger area of the skin surface of the user and/or over a larger extent of a base plate to be attached to the complementary-material element 22.

Figure 10B:
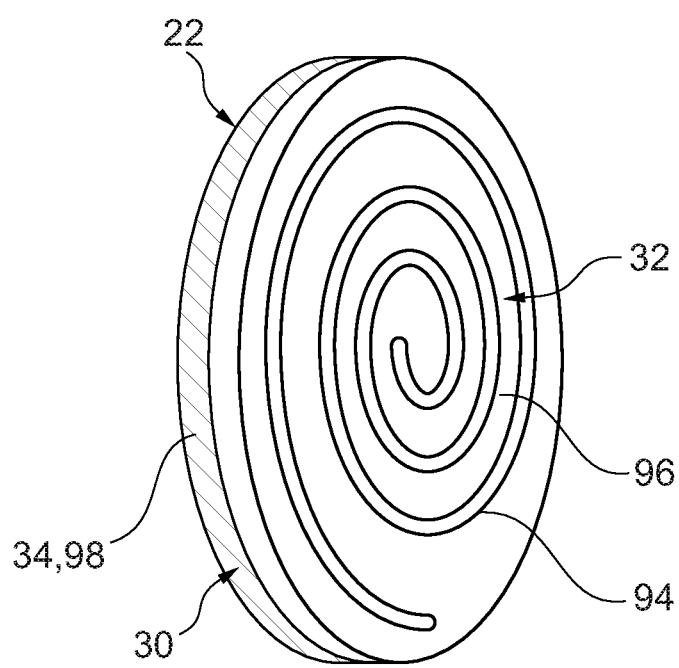
FIG. 10B is a perspective view of one embodiment of a complementary-material element including a first entity formed in a layered relationship with a second entity.

FIG. 10B is a schematic perspective view of one embodiment of a complementary-material element 22 including a first entity 30 formed in a layered relationship with a second entity 32 including two different material compositions 94, 96 being spirally wound together to form two neighbouring zones of material in the shape of an Archimedean spiral. In embodiments according to the illustration of FIG. 10B, a first material composition 34 of the first entity 30 advantageously includes a paste material 98, and the two different material compositions 94, 96 of the second entity 32 advantageously include at least two different neutralizers or neutralizing components. Further advantageously, each of the neutralizers is provided in each their zone forming the shape of the Archimedean spiral in FIG. 10B. This provides for improved distribution of more than one type of neutralizer material.

Figure 11:
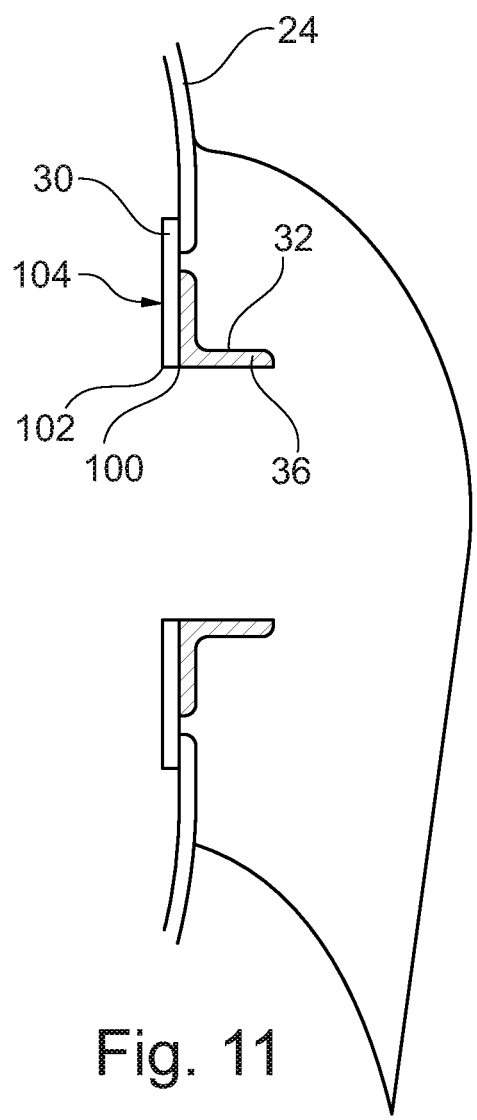
FIG. 11 is a cross-sectional view of one embodiment of a complementary-material element attached to a base plate of an ostomy appliance.

FIG. 11 is a schematic cross-sectional view of one embodiment of a complementary-material element 22 attached to a base plate 24 of an ostomy appliance. In embodiments illustrated by FIG. 11, an intermediate film material 100 is provided between a first entity 30 and a second entity 32 of the complementary-material element 22. The second entity 32 includes a second material composition 36 which is mouldable, allowing the second entity 32 to configure with a 90-degree angle for creating extra protection from stomal output exuding from a stoma. Additionally, or alternatively, embodiments of a complementary-material element 22 as illustrated in FIG. 11 includes an intermediate film 102 provided between an adhesive material element 104 and the first entity 30. Thereby, the adhesive material element 104 is separated from the first material composition of the first entity 30. Particularly, the intermediate film material 102 additionally protects the adhesive material element 104 from moisture of the stomal output, especially during release of the neutralizing component from the second material composition 36 of the second entity 32. In embodiments, the intermediate film 100 is configured to be engageable with the adhesive on the proximal surface of the base plate 24 in a strong adhesive bond. In the embodiment of FIG. 11, the strong adhesive bond is configured at a radially outermost portion of the first entity 30. However, the first entity 30 can also be configured to co-extend with the base plate 24, such that a major surface portion of the first entity 30 with the intermediate film 100 on it, is available for strong adhesive bonding to the proximal surface of the base plate 24. This is particularly, but not exclusively, useful for ensuring that the complementary-material element 22 is easily removable from the skin of the user, when the ostomy appliance 20 needs to be exchanged for a fresh one.

With additional reference to FIG. 1, further illustrated is one embodiment of the components of a kit of parts 16 including a complementary-material element 22 as disclosed in this disclosure, a base plate 24 and a collecting bag 26 of an ostomy appliance 20. The base plate 24 comprises an adhesive 18 provided on a first surface of a carrier film 21. The second surface of the carrier film 21 is formed by the carrier film itself. The collecting bag 26 can be detachably or permanently attachable to the base plate 24 via a coupling or attachment arrangement 25.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

The invention claimed is:

1. An ostomy appliance comprising:
   a base plate, and
   a complementary-material element separate from and attachable to the base plate of the ostomy appliance, where the base plate comprises a stoma opening, a carrier film, and an adhesive deposited on a proximal side of the carrier film for securing the base plate to skin of a user, with the complementary-material element adapted for
   placement between the adhesive of the base plate and the skin of the user and comprising:
      at least a first entity coupled to a second entity, with the first entity
      comprising a first material composition and the second entity comprising a
      second material composition different from the first material composition;
   wherein the first entity and the second entity are layer with the first entity proximal to a first portion of the second entity;
   wherein the first material composition of the first entity is configured to be resistant to erosion to physically protect the adhesive on the proximal side of the carrier film and the skin of the user from stomal output;
   the second material composition comprises a neutralizer dispersed as neutralizer particles in a matrix of the second material composition;
   wherein the second material composition of the second entity is configured to erode in response to the stomal output;
   wherein the neutralizer particles are releasable from the complementary-material element and into the stoma opening in response to the stomal output to neutralizer the stomal output and reduce damaging effects of the stomal output to the skin of the user.

2. The ostomy appliance of claim 1, wherein the first entity comprises adhesive.

3. The ostomy appliance of claim 1, wherein the first entity comprises an adhesive layer defining an external surface the first entity.

4. The ostomy appliance of claim 1, wherein the first entity comprises adhesive and the ostomy appliance further comprises an intermediate film provided between the adhesive and the second entity.

5. The ostomy appliance of claim 1, wherein the first entity is proximal to the first portion of the second entity and arranged alongside of a second portion of the second entity.

6. The ostomy appliance of claim 1, wherein the first entity is proximal to the first portion of the second entity and a second portion of the second entity is surrounded by the first entity.

7. The ostomy appliance of claim 1, wherein the second entity forms a centre portion of the complementary-material element and the first entity forms a peripheral portion of the complementary-material element.

8. The ostomy appliance of claim 1, wherein the releasable neutralizer particles are adapted to form a gel upon contact with moisture.

9. The ostomy appliance of claim 1, wherein the first material composition is a paste.

10. The ostomy appliance of claim 1, wherein further comprising:
a separation element located between the first material composition and the second material composition.

11. The ostomy appliance of claim 1, wherein the neutralizer particles comprises clay.

12. The ostomy appliance of claim 1, wherein the neutralizer particles comprises a potato protein.

13. The ostomy appliance of claim 1, wherein an entirety of the first particles entity is proximal to the second entity.

14. The ostomy appliance of claim 1, wherein the complementary-material element is ring-shaped provided with a central opening adapted for placement around the stoma opening of the base plate.

15. The ostomy appliance of claim 1, wherein the first entity of the complementary-material element provides a first ring-shaped portion and the second entity of the complementary-material element provides a second ring-shaped portion that is embedded in a distal side of the first ring shaped portion.

16. The ostomy appliance of claim 1, wherein the complementary-material element is ring-shaped and provided with a central opening;
wherein the first entity of the complementary-material element provides a first ring-shaped portion and the second entity of the complementary-material element provides a second ring-shaped portion that is embedded into the first entity and deposited around the central opening;
wherein the second entity is exposed within the central opening of the complementary-material element.

* * * * *